(12) United States Patent
Zehbe et al.

(10) Patent No.: US 7,947,077 B2
(45) Date of Patent: May 24, 2011

(54) METHOD OF PRODUCING A COMPOSITE MATERIAL, A COMPOSITE MATERIAL SO PRODUCED AND ITS APPLICATION

(75) Inventors: Rolf-Dieter Zehbe, Berlin (DE); Helmut Schubert, Berlin (DE)

(73) Assignee: Dritte Patentportfolio Beteiligungsgesellschaft mbH & Co. KG, Schonefeld/Waltersdorf (DE)

( * ) Notice: Subject to any disclaimer, the term of this patent is extended or adjusted under 35 U.S.C. 154(b) by 1021 days.

(21) Appl. No.: 10/578,111

(22) PCT Filed: Nov. 5, 2004

(86) PCT No.: PCT/EP2004/012564
§ 371 (c)(1),
(2), (4) Date: Apr. 11, 2007

(87) PCT Pub. No.: WO2005/044325
PCT Pub. Date: May 19, 2005

(65) Prior Publication Data
US 2007/0282439 A1 Dec. 6, 2007

(30) Foreign Application Priority Data
Nov. 5, 2003 (DE) .................. 103 51 661

(51) Int. Cl.
*A61L 27/46* (2006.01)
*A61L 27/56* (2006.01)
*C12N 5/00* (2006.01)
*B32B 3/26* (2006.01)

(52) U.S. Cl. ..................... 623/16.11; 205/665; 428/304; 435/325

(58) Field of Classification Search ........................ None
See application file for complete search history.

(56) References Cited

U.S. PATENT DOCUMENTS

| 3,892,649 A | 7/1975 | Phillips et al. |
| 4,955,893 A | 9/1990 | Yannas et al. |
| 5,885,829 A * | 3/1999 | Mooney et al. ............... 435/325 |
| 6,417,247 B1 | 7/2002 | Armstrong et al. |
| 6,447,701 B1 | 9/2002 | Heschel et al. |
| 6,464,672 B1 * | 10/2002 | Buckley ........................ 604/304 |
| 2006/0134599 A1 * | 6/2006 | Toner et al. ........................ 435/4 |

FOREIGN PATENT DOCUMENTS

| DE | 3910314 | 11/1989 |
| WO | WO 03/022319 | 3/2003 |
| WO | WO 03/089022 | 10/2003 |

OTHER PUBLICATIONS

Kreklau B; et al, Tissue engineering of biphasic joint cartilage transplants, Biomaterials, Elsevier Science Publishers BV., vol. 20, No. 18, pp. 1743-1749, Sep. 1999.
Mikos A G, et al., Formation of highly porous biodegradable scaffolds for tissue engineering, EJB Electronic Journal of Biotechnology, vol. 3, No. 2, pp. 1-12, Aug. 15, 2000.
Zehbe R at al., Colagen-based/hydroxyapatite matrices for articular cartilage replacement, Key Engineering Materials, vol. 254-256, pp. 1083-1086, Nov. 7, 2003.

* cited by examiner

*Primary Examiner* — Herbert J. Lilling
(74) *Attorney, Agent, or Firm* — Pearl Cohen Zedek Latzer, LLP

(57) ABSTRACT

The invention relates to a method for producing a composite material, to a composite material produced according to said method and to the use of said material.

31 Claims, 2 Drawing Sheets

A

B

METHOD OF PRODUCING A COMPOSITE MATERIAL, A COMPOSITE MATERIAL SO PRODUCED AND ITS APPLICATION

FIELD OF THE INVENTION

The present invention relates to a method of producing a composite material, a composite material so produced and its application.

BACKGROUND OF THE INVENTION

In the medical field, more and more synthetic tissue substrates are required to replace organs and tissue. This field is commonly referred to as tissue engineering. Tissue substrates that broadly correspond to the native organ or tissue as far as its biological, biochemical, biomechanical and structural properties are concerned are of particular significance. In reconstructive and regenerative medicine, traumatology and orthopedics tissue substrates in the musculo-skeletal field (a substitute for bones, cartilage and tendons) have become particularly important during the last few years. In many ways, the properties of currently available substrates do not correspond to native tissue because frequently the natural morphology is not reproduced and/or biochemical and/or biomechanical properties do not match. Tissue engineering represents a promising therapeutic approach for the repair of osteochondral defects. In this process, cells with a potential of building cartilage are incorporated into porous supporting materials and then placed in vivo into the chondral defect— directly or after in vitro pre-cultivation. For their application, these supporting materials have to meet specific requirements, particularly stability of shape, retarded decomposition, bio-compatibility, cell adherence, chondro-conductivity. The field of diseases of the joints is of particular medical and economic significance. In this medical field, the most painful conditions are those in which cartilage and the bone structure underneath have been destroyed. Cartilage has a limited ability of regeneration and normally an inferior quality compared against healthy cartilage. Numerous attempts have been made to transplant healthy cartilage and subchondral bone tissue or to keep it in cultures; however, no appropriate substitute has been created so far with such an approach.

In order to be able to use synthetic materials as appropriate substitute of cartilage numerous different properties of the natural system have to be taken into consideration. These properties include the biochemical composition, the structural identity (imitation of zonal morphology) and biomechanical properties. Different authors have suggested that porous foams on the basis of natural and synthetic polymers should be used for these materials. Mikos et al., Electronic Journal of Biotechnology, Vol. 3 No. 2, 2000 present a good overview on the technologies for the production of porous materials for tissue engineering. The authors describe several methods of producing highly porous lattice structures. Lattice structures are produced, for instance, by way of creating a three-dimensional network of fibers of poly-glycolic acid ("fiber bonding"). Another method of producing pores in a matrix includes the use of a water-soluble porogen, like, for instance, a salt. In this case, a polymer, poly-lactic acid or poly(DL-lactic-co-glycolic acid) is dissolved in chloroform or dichloromethane and then poured into a Petri culture dish filled with the porogen. During this process, the porogen diffuses into the polymer matrix. After vaporization of the solvent, the polymer/porogen composite is placed in water for two days to eliminate the porogen. The porosity of the resulting lattice can be controlled by the quantity of the porogen added while the pore size depends on the size of the porogen particles, e.g. when the porogen is a salt, the size of the salt crystals. A further method avoiding the use of organic solvents during pore formation is the use of a gas as porogen. In this process, solid sheets of a polymer are molded and then exposed to a gas, e.g. $CO_2$, at an elevated pressure for a rather long period of time. Thus porosities of up to 93% and pore sizes up to 100 μm are obtained in which case the pores, however, are not connected with each other. Additional techniques that have been suggested for the production of porous polymer lattices are based on the concept of phase separation instead of incorporating a porogen. Such methods include emulsification/freeze drying or a liquid-liquid phase separation. In the first method, a polymer is dissolved, for instance in dichloromethane, then distilled water is added in order to form an emulsion. The polymer/water mixture is poured into a mold and quenched by introducing it into liquid nitrogen. After quenching, the lattice structures so created are freeze-dried at −55° C., which leads to the elimination of dispersed water and the polymer solvent. The liquid-liquid phase separation produces high-polymeric and low-polymeric phases within a polymer solution. The low-polymeric phase is now eliminated, leaving a highly porous polymeric network.

Yannas and collaborators propose a technique for phase separation of a hydrogel (U.S. Pat. No. 4,955,893). An aqueous suspension of collagen glycosamino glycane is frozen in a test tube in axial direction along the tube in a way that ice crystals may form. Afterwards the frozen material is exposed to a vacuum under sublimation conditions such that the ice crystals so formed sublimated and left an oriented porous channel structure suitable for the subsequent population of growing nerve cells. A similar technique is described in the U.S. Pat. No. 6,447,701 (Herschel et al.) wherein the polymer suspension is applied between two surfaces of different temperatures and wherein the surfaces oppose each other and wherein—due to the different temperatures—an essentially well-ordered or homogeneous structure of the polymer network and the crystals that are formed therein is created.

Neither technology as described in prior art has so far resulted in the production of a satisfactory substrate material that equally meets the requirements in terms of its biochemical composition, the zonal morphology and the biomechanical properties.

In accordance therewith, the present invention has been based on the problem of providing a method of producing composite materials that can be used as bone/cartilage substitute and that exhibit a tissue morphology resembling the natural tissue, that are bio-compatible and display an excellent congruence with native tissue in terms of both their biomechanical and their biochemical properties.

In addition, it has been the object of the present invention to provide a corresponding method that is easy to carry out.

Another problem of the present invention was the provision of a composite material which excellently imitates particularly the zonal morphology of natural tissue material, especially of cartilage/bone tissue.

SUMMARY OF THE INVENTION

These problems are solved by a method of producing a composite material, which comprises the following steps:
a) providing a hydrogel containing at least one further component that precipitates or forms a solid phase when an electrical field is applied to said hydrogel,
b) applying an electrical field to said hydrogel, c) inducing a structuring operation, preferably a pore formation operation, in said hydrogel.

In one embodiment, the steps b) and c) are carried out together in view of time, one before or after the other, or in such a manner that one of the two steps is started after the respective other one has commenced but before the other step has been completed.

Step c) is preferably carried out by freezing the hydrogel and/or freeze-drying the hydrogel and/or by electrolysis of water and/or electrolysis of aqueous solutions in the hydrogel.

In one embodiment, step b) is carried out by means of at least two electrodes of opposite polarity.

In one embodiment, said at least one further component, which precipitates or which forms a solid phase when an electrical field is applied to the hydrogel, forms a crystalline and/or amorphous phase or a combination of crystalline and amorphous phases in step b).

Preferably, a voltage of 3 V to 20 V is applied to the hydrogel and/or an electric current of an amperage of 0.5 A to 5 A flows through the hydrogel, preferably over a period of 0.5 minutes to 120 minutes.

The voltage is a direct voltage or an alternating voltage. In one embodiment, the alternating voltage has a frequency in the range between 1 Hertz to 0.01 Hertz.

In one embodiment, the hydrogel is a hydrogel of one or more compounds selected from the group that comprises collagen, in particular type I and type II collagen, telopeptide-free collagen, collagen hydrolysates, proteoglycanes, glycosamino glycanes, polymethacrylic acids, polymethacrylates, polyvinyl pyrrolidone, polyvinyl alcohol, gelatin, polyglycolic acid, polylactic acid, copolymers of polylactic acid and polyglycolic acid, glucose, lipids, phospholipids, urates, hyaluronic acid, derivatives of hyaluronic acid, in particular esters of hyaluronic acid as well as ionic components selected from the group comprising $Na^+$, $K^+$, $Mg^{2+}$, $Ca^{2+}$, $Cl^-$, $HCO_3^-$, $HPO_4^{2-}$, $SO_4^{2-}$, $F^-$.

In one embodiment, the at least one further component that precipitates or forms a solid phase when an electrical field is applied to the hydrogel is selected from the group comprising calcium carbonates, calcium phosphates, in particular hydroxyl apatite, tri-calcium phosphates, brushite, octa-calcium phosphate, amorphous calcium phosphate, tetra calcium phosphate, monetite, calcium-deficient hydroxyl apatite as well as compounds formed of ionic components selected from the group comprising $Na^+$, $K^+$, $Mg^{2+}$, $Ca^{2+}$, $Cl^-$, $HCO_3^-$, $HPO_4^{2-}$, $SO_4^{2-}$, $F^-$ as well as ionic components.

In one embodiment, the hydrogel comprises a component which is electrically conductive, with this component being identical to or different from said at least one further component which precipitates or forms a solid phase when an electrical field is applied to the hydrogel.

The electrically conductive component is preferably incorporated into the hydrogel or applied to the hydrogel.

In one embodiment, the electrically conductive component is chemically and/or biologically inert, in which case it is preferred that the electrically conductive component is selected from the group comprising precious metals, in particular elementary gold and/or platinum, as well as carbon, especially graphite.

Provided that the electrically conductive component is incorporated into the hydrogel it is preferably distributed homogeneously or non-homogeneously in the hydrogel.

If the electrically conductive component is applied to a surface of the hydrogel it is preferably structured by way of a surface treatment.

In one embodiment, the hydrogel is present as a layer wound up before or after realization of step b) and/or step c).

Preferably, the hydrogel is chemically and/or physically cross-linked.

In one embodiment, freeze-drying is performed by freezing the hydrogel to a temperature in the range between −1° C. and −196° C., preferably in the range between −10° C. and −50° C. with subsequent sublimation.

In one embodiment, the freezing of the hydrogel is carried out in a directional and/or non-directional mode, preferably from one and/or several sides of the hydrogel, with the freezing of the hydrogel preferably taking place over a period of approximately thirty minutes to four hours. An example of non-directional freezing is very rapid solidification (shock-freezing operation) which leads to an amorphous, vitreous state of the hydrogel.

The problems of the invention are also solved by a composite material produced in a method according to the present invention.

In one embodiment, the composite material of the present invention is provided with a pore-containing layer of a gel, preferably a partially hydrated hydrogel or a xerogel to which a solid phase, preferably a crystalline and/or amorphous phase or a combination of crystalline and/or amorphous phases is/are linked, with the preferred pore size ranging from 10 μm to 150 μm.

As used in this context, "pore size" defines the mean pore channel diameter.

In one embodiment, the solid, preferably crystalline and/or amorphous phase or the combination of crystalline and/or amorphous phases, is a calcium phosphate.

In one embodiment, the composite material of the present invention further comprises at least one substance promoting the cell growth or cell colonization or cell adhesion, which is preferably a growth factor or a fetal serum or poly-L lysine. In one embodiment, the composite material comprises serum, with the serum being of autogenous, syngenous, allogenous or xenogenous origin.

In a preferred embodiment, the at least one substance promoting cell growth or cell colonization or cell adhesion, is a serum which is of autogenous, syngenous, allogenous or xenogenous origin. In a more strongly preferred mode, the growth factor is selected from the group comprising substances of the TGF-β super family, in particular TGF-β1. In one embodiment, the fetal serum is an animal fetal serum, for example fetal calf serum.

In one embodiment, the composite material further comprises biological cells, preferably human or animal cells.

In another embodiment, the composite material comprises plant cells.

The problems of the invention are also solved by the use of a composite material according to the present invention as carriers for biological cells, preferably human or animal or plant cells.

Furthermore, the problems of the present invention are solved by the use of a composite material according to the present invention as tissue substitute in the body of a human or an animal being.

Furthermore, the problems of the invention are solved by the use of a composite material according to the present invention as a substrate material for carrying biologically and/or chemically and/or catalytically active substances in the fields of sewage treatment, filtration, bioreactor technology and/or catalysis.

As used in this context, the term "hydrogel" refers to a gel that contains water and is based on hydrophilic molecules, preferably polymers, which occur as three-dimensional networks. In water, these networks swell up to an equilibrium volume, largely maintaining its shape. The networks are formed predominantly via chemical bonding of the individual polymer chains; it is, however, also physically feasible via electrostatic, hydrophobic or dipole/dipole interactions between individual segments of the molecular chains.

As used in this context, the term "xerogel" denotes gels that have lost their liquidity in one way or another, for example through vaporization, squeezing or suction; in this process, the three-dimensional structure of the network may have changed with the result that the distances between the structural elements have dimensions different from the dimensions in the hydrogel.

As used in this context, the general term "gels" is defined as dimensionally stable, easily deformable disperse systems rich in liquids and/or gases, which are constituted by at least two components consisting mostly of a solid substance in colloidal distribution, having long or strongly branched particles and a liquid (usually water) as a dispersing agent. As a rule, the solid substance is coherent, which means that it forms a three-dimensional network in the dispersing agent, with the particles adhering to each other at different sites by primary and secondary valences.

An electrical field may be applied to the hydrogel of the present invention via electrodes of a design known per se. In a preferred embodiment, two electrodes are used which contact the hydrogel in an electrically conducting manner on opposite sides of the hydrogel. The technique of freeze-drying the hydrogel is known per se and is described in prior art (e.g. in the U.S. Pat. No. 4,955,893). The hydrogel-freezing step is preferably carried out in an oriented manner so that ice crystals are formed in a cellular and/or dendritically structured manner and/or in a way predetermined by the physical laws governing the solidification of aqueous substances. The freezing step may, however, also be carried out in a non-oriented manner. One example of non-oriented freezing is a very rapid solidification (shock freezing operation), for instance through a period of 1 second to 180 seconds, which results in an amorphous vitreous state of the hydrogel.

In a preferred embodiment, the hydrogel is bonded in a covalent manner to the solid phase then forming of the at least one further component. This may happen, for instance, via chemical cross-linkage or physical cross-linkage. The physical cross-linkage can be realized by radiation (usually short-wave radiation such as UV, gamma, X-ray) and/or by thermal treatment. The action pattern is basically similar to the pattern in chemical cross-linkage (reactive chemical groups or molecules that form chemical bonds with other molecules or groups, thus causing the structure to stabilize).

In a preferred embodiment, the electrically conductive component contained in the hydrogel is biocompatible.

In the following, reference will now be made to the illustrations wherein:

BRIEF DESCRIPTION OF THE DRAWINGS

Illustration 1 represents a set-up for the production of one embodiment of a composite material according to the present invention, Illustration 2A shows an embodiment of a composite material produced according to the method of the present invention, Illustration 2B shows another embodiment of a composite material produced according to the method of the present invention, wherein the cell-histological image of cartilage dyed with hematoxylin eosin is superimposed on the composite material. The smaller frame inserted in illustration 2B shows the composite material according to the present invention whereas the larger frame in illustration 2B shows the natural cartilage. Cell bodies in the cartilage can be seen as dark corpuscles dyed with hematoxylin eosin. The superimposition of the images shows the proper congruence between the composite material of the present invention and the natural structure of the healthy cartilage.

DETAILED DECRIPTION OF THE INVENTION

Figure 1:
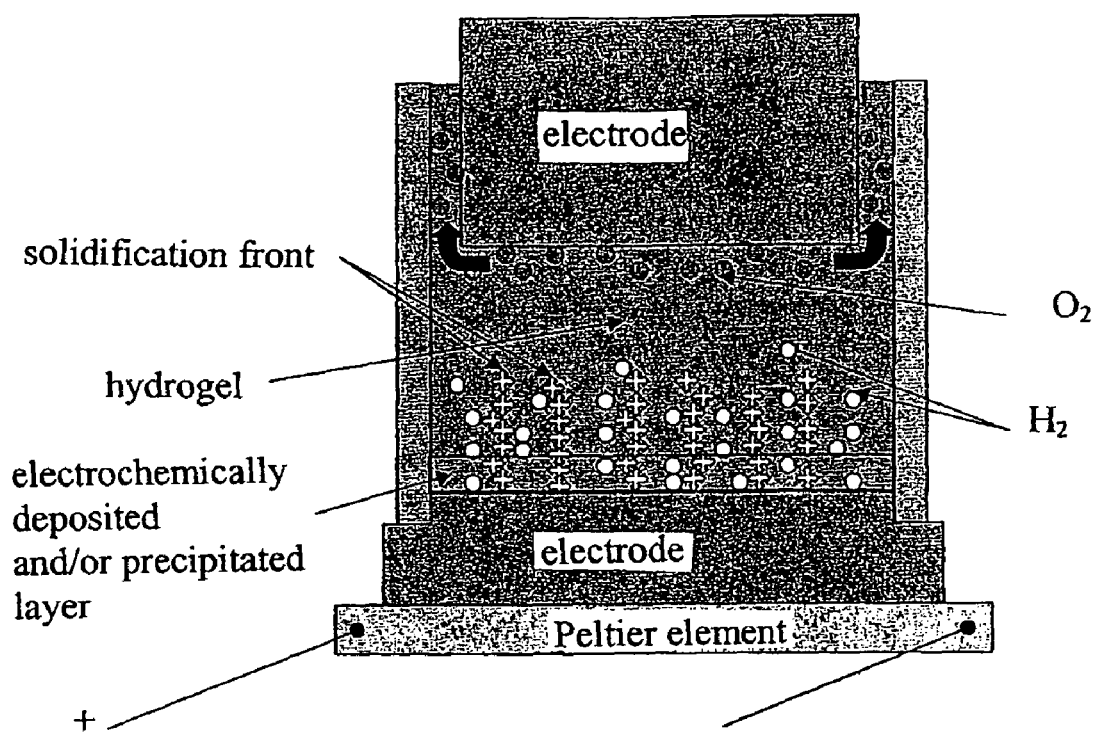
Figure 2:
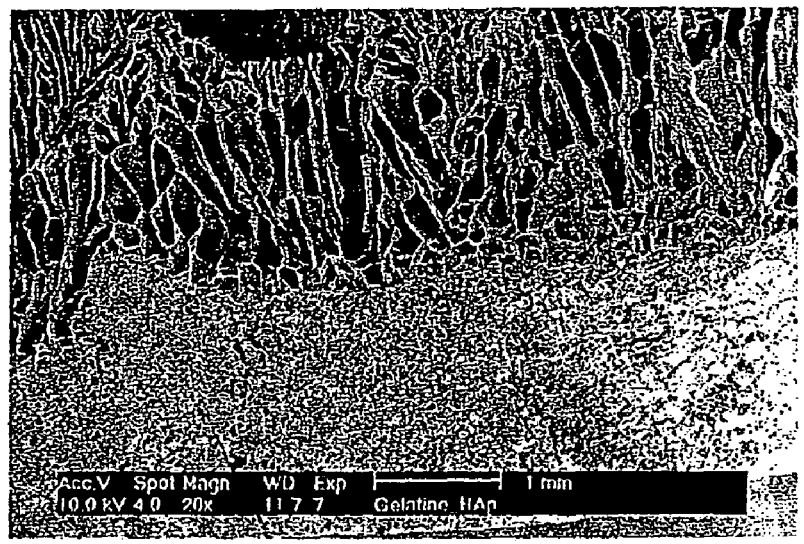
Figure 2:
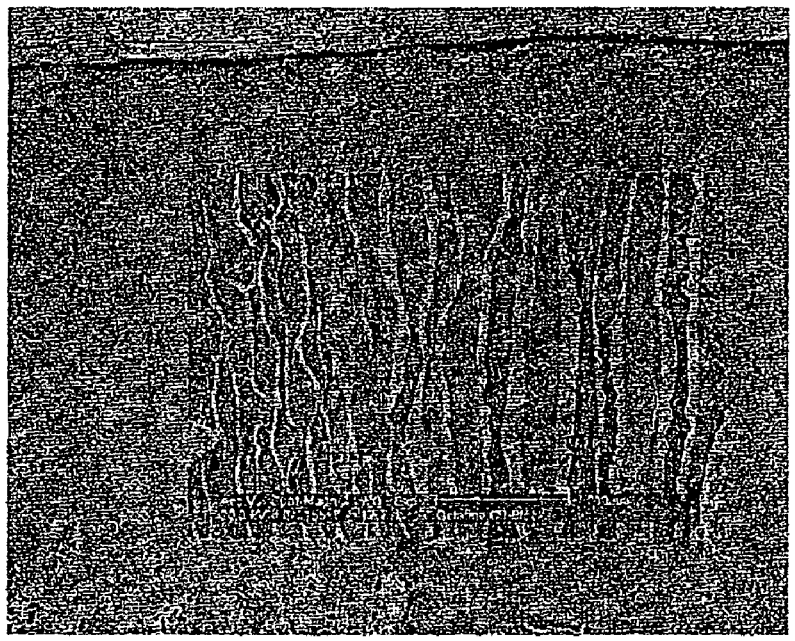

The invention will now be described on the basis of the following examples described here for explanation rather than for a restriction of the invention.

EXAMPLE 1

The experimental arrangement consisting of a Peltier element and an appertaining cooling body as well as two platinum electrodes and the jacket of the cylindrical sample receptacle is subjected to sterilizing pre-treatment. Both platinum electrodes—whereof one electrode forms the bottom of the sample receptacle—are sterilized together with a PTFE tube that forms the jacket of the cylindrical sample receptacle in a pressurized autoclave under a saturated-steam atmosphere at 121° C. and at a maximum pressure of 3 bar for 30 minutes. Other sterilization processes common in medicine may equally be applied.

The Peltier element, which is used as a cooling and heating body, is heated to 40° C. by appropriate polarization at the surface that is in contact with the sample receptacle.

5 g gelatin (Sigma, type A of pig skin) is homogeneously dissolved in 40 ml of a saturated calcium phosphate solution at 50° C. 5 ml of the gelatin solution are subsequently charged into the sterile sample receptacle of the test apparatus. When the gelatin solution has been charged, the upper platinum electrode is dipped into the solution.

Subsequently, the following steps are carried out:

1 a) The polarity of the Peltier element is reversed so as to adjust a temperature of −30° C. at the surface which is in contact with the sample receptacle. At the same time, a voltage of 15 V is adjusted at the platinum electrodes, which causes the electrolytic decomposition of the water and the formation of gas bubbles of $H_2$ and $O_2$. In addition, a calcium phosphate layer forms at the bottom electrode. As soon as a compact layer of ice forms at the electrode constituting the bottom of the sample receptacle the formation of gas discontinues because the flow of current is no longer possible.

1b) In opposition to step 1a), the water undergoes electrolytic decomposition as early as prior to the reversal of the polarity of the Peltier element (and the ensuing drop of temperature to −30° C.) and discontinues only as soon as a compact layer of ice has formed.

Subsequently to the alternative steps 1a) or 1b), the solution will have solidified in a completely oriented structure after 2 hours, approximately, and is then pressed with a sterile punch out of the jacket of the sample receptacle and is then immediately transferred to a freeze drier. After 12 hours of dry-freezing, the dried hydrogel is taken out of the freeze drier.

1c) The dried hydrogel is chemically cross-linked in an aldehyde-containing atmosphere for 6 hours. Afterwards, three washing cycles are carried out in a sterile 0.9% saline solution in order to eliminate aldyhyde residues in the dried hydrogel.

1d) The dried hydrogel is thermally cross-linked in a dry atmosphere at 120° C.

A composite material produced within the scope of this example can be seen in illustrations 1, 2A and 2B (small frame).

EXAMPLE 2

Properties of the composite material according to the present invention as in Example 1.

2a) The mechanical properties of the composite material according to the present invention were tested in a special experimental arrangement.

The properties of the material have been determined as follows:

| Literature | Remarks | E-module [MPa] | Poisson number |
|---|---|---|---|
| Korhonen et al., J. Biomech., 903-909, 2002 | (Test die Ø = 3.7 mm) bovine explants | | |
| | Femur | 0.47 ± 0.15 | 0.26 ± 0.08 |
| | Humerus | 1.15 ± 0.43 | 0.16 ± 0.06 |
| | Patella | 0.72 ± 0.19 | 0.21 ± 0.05 |
| Composite material according to the invention | (Test die Ø = 8.0 mm) composite material according to the invention | 0.67 ± 0.02 | 0.27 |

The E module defines the modulus of elasticity, a material-specific parameter. It represents the factor of proportionality in the context known as Hooke's Law. The Poisson number denotes the transverse contraction which defines the ratio between the change of the cross-section and the change of the length of a material.

Mechanical testing was performed in a 0.9% saline solution. The mechanical properties of the composite material according to the present invention range closely to those of natural tissue.

2b) The diameters of the pore channels formed in the composite material according to the present invention were determined by evaluating SEM images. The adjustable pore channel diameter ranges between 10 µm and 150 µm and promotes a simple colonization of cells in the pore channels as well as a good nutritive supply of the cells by way of diffusion. During cell colonization, a cell suspension is incorporated into the composite material according to the present invention and the cells so colonized form the very dense natural fiber structure later on, which is similar to the one found in healthy cartilage. Thus the composite material according to the present invention permits the formation of natural cartilage/bone tissue in an excellent manner, presents a similar tissue morphology after colonization, displays an excellent convergence with native tissue in terms of its biomechanical properties and is biocompatible.

The characteristics of the invention as disclosed in the above description, the patent claims and the drawings may be essential for the realization of the invention in its different embodiments, both individually and in any combination whatsoever.

The invention claimed is:

1. Method of producing a composite material, which comprises the following steps:
   a) providing a hydrogel containing at least one further component that precipitates or forms a solid phase when an electrical field is applied to said hydrogel,
   b) applying an electrical field to said hydrogel,
   c) inducing a structuring operation, comprising a pore formation operation, in said hydrogel.

2. Method according to claim 1, in which the steps b) and c) are carried out together in view of time, one before or after the other, or in such a manner that one of the two steps is started after the respective other one has commenced but before the other step has been completed.

3. Method according to claim 1, characterized in that step c) is carried out by freezing the hydrogel and/or freeze-drying the hydrogel and/or by electrolysis of water and/or by electrolysis of aqueous solutions in the hydrogel.

4. Method according to claim 1, characterized in that step b) is carried out by means of at least two electrodes of opposite polarity.

5. Method according to claim 1, characterized in that in step b) said at least one further component, which precipitates or which forms a solid phase when an electrical field is applied to the hydrogel, forms a crystalline and/or amorphous phase or a combination of crystalline and amorphous phases.

6. Method according to claim 1, characterized in that in step b) a voltage of 3 V to 20 V is applied to the hydrogel and/or an electric current of an amperage of 0.5 A to 5 A flows through the hydrogel.

7. Method according to claim 6, characterized in that the applied voltage is a direct voltage or an alternating voltage.

8. Method according to claim 1, characterized in that the hydrogel is a hydrogel of one or more compounds selected from the group that consists of collagen, telopeptide-free collagen, collagen hydrolysates, proteoglycanes, glycosamino glycanes, polymethacrylic acids, polymethacrylates, polyvinyl pyrrolidone, polyvinyl alcohol, gelatin, polyglycolic acid, polylactic acid, copolymers of polylactic acid and polyglycolic acid, glucose, lipids, phospholipids, urates, hyaluronic acid, derivatives of hyaluronic acid, and ionic components selected from the group consisting of $Na^+$, $K^+$, $Mg^{2+}$, $Ca^{2+}$, $Cl^-$, $HCO_3^-$, $HPO_4^{2-}$, $SO_4^{2-}$, and $F^-$.

9. Method according to claim 1, characterized in that said at least one further component that precipitates or forms a solid phase when an electrical field is applied to the hydrogel is selected from the group consisting of calcium carbonates, calcium phosphates, in particular hydroxyl apatite, tri-calcium phosphates, brushite, octa-calcium phosphate, amorphous calcium phosphate, tetra calcium phosphate, monetite, calcium-deficient hydroxyl apatite, as well as compounds formed of ionic components selected from the group consisting of $Na^+$, $K^+$, $Mg^{2+}$, $Ca^{2+}$, $Cl^-$, $HCO_3^-$, $HPO_4^{2-}$, $SO_4^{2-}$, and $F^-$.

10. Method according to claim 1, characterized in that the hydrogel comprises a component which is electrically conductive, with this component being identical to or different from said at least one further component which precipitates or forms a solid phase when an electrical field is applied to the hydrogel.

11. Method according to claim 10, characterized in that the electrically conductive component is incorporated into the hydrogel or applied to the hydrogel.

12. Method according to claim 1, characterized in that the electrically conductive component is chemically and/or biologically inert.

13. Method according to claim 12, characterized in that the electrically conductive component is selected from the group consisting of precious metals and carbon.

14. Method according to claim 11, characterized in that the electrically conductive component is incorporated into the hydrogel and is there distributed homogeneously or non-homogeneously.

15. Method according to claim 11, characterized in that the electrically conductive component is applied to a surface of the hydrogel, and is structured by way of a surface treatment.

16. Method according to claim 1, characterized in that the hydrogel is present as a layer wound up before or after realization of step b) and/or step c).

17. Method according to claim 1, characterized in that the hydrogel is chemically and/or physically cross-linked.

18. Method according to claim 3, characterized in that freeze-drying is performed by freezing the hydrogel to a temperature in the range between −1° C. and −196° C. with subsequent sublimation.

19. Method according to claim 18, characterized in that the freezing of the hydrogel is carried out in a directional and/or non-directional mode.

20. Method according to claim 18, characterized in that the freezing of the hydrogel takes place over a period of approximately thirty minutes to four hours.

21. Composite material produced by a method according to claim 1.

22. Composite material according to claim 21, characterized by a pore-containing layer of a gel to which a solid phase in linked.

23. Composite material according to claim 21, characterized by a pore size ranging from 10 μm to 150 μm.

24. Composite material according to claim 21, characterized in that the solid phase is a calcium phosphate.

25. Composite material according to claim 21, further comprising at least one substance promoting cell growth or cell colonization or cell adhesion.

26. Composite material according to claim 25, characterized in that said at least one substance promoting cell growth or cell colonization or cell adhesion is a growth factor or a fetal serum or poly-L lysine, the growth factor being selected from the group comprising substances of the TGF-β super family, and the fetal serum being an animal fetal serum.

27. Composite material according to claim 25, characterized in that said at least one substance promoting cell growth or cell colonization or cell adhesion, is a serum which is of autogenous, syngenous, allogenous or xenogenous origin.

28. Composite material according to claim 21, characterized in that it further comprises biological cells.

29. The composite material according to claim 21, wherein said material is used as a substrate material for carrying biological cells.

30. The composite material according to claim 21, wherein said material is used as tissue replacement in human or animal bodies.

31. The composite material according to claim 21, wherein said material is used as a substrate material for carrying biologically and/or chemically and/or catalytically active substances in the fields of sewage treatment, filtration, bioreactor technology and/or catalysis.

* * * * *